(12) United States Patent
Gainer

(10) Patent No.: US 8,901,174 B2
(45) Date of Patent: Dec. 2, 2014

(54) USE OF BIPOLAR TRANS CAROTENOIDS AS A PRETREATMENT AND IN THE TREATMENT OF PERIPHERAL VASCULAR DISEASE

(75) Inventor: John L. Gainer, Charlottesville, VA (US)

(73) Assignee: Diffusion Pharmaceuticals LLC, Charlottesville, VA (US)

( * ) Notice: Subject to any disclaimer, the term of this patent is extended or adjusted under 35 U.S.C. 154(b) by 0 days.

(21) Appl. No.: 13/137,322

(22) Filed: Aug. 5, 2011

(65) Prior Publication Data

US 2012/0035256 A1    Feb. 9, 2012

Related U.S. Application Data

(62) Division of application No. 12/081,236, filed on Apr. 11, 2008.

(60) Provisional application No. 60/907,718, filed on Apr. 13, 2007.

(51) Int. Cl.
*A61K 31/19* (2006.01)
*A61K 31/015* (2006.01)

(52) U.S. Cl.
CPC .................................. *A61K 31/015* (2013.01)
USPC ....................................................... 514/574

(58) Field of Classification Search
CPC .... A61K 31/19; A61K 31/194; A61K 31/195
USPC ......................................................... 514/574
See application file for complete search history.

(56) References Cited

U.S. PATENT DOCUMENTS

| | | | |
|---|---|---|---|
| 2,175,843 | A | 10/1939 | Kuhn et al. |
| 2,948,748 | A | 8/1960 | Guex et al. |
| 3,489,806 | A | 1/1970 | Gutmann et al. |
| 3,687,990 | A | 8/1972 | Gutmann et al. |
| 3,853,993 | A | 12/1974 | Gainer et al. |
| 3,965,261 | A | 6/1976 | Gainer |
| 3,975,519 | A | 8/1976 | Gainer |
| 4,009,270 | A | 2/1977 | Gainer, Jr. |
| 4,038,144 | A | 7/1977 | Gainer |
| 4,046,880 | A | 9/1977 | Gainer |
| 4,070,460 | A | 1/1978 | Gainer, Jr. |

(Continued)

FOREIGN PATENT DOCUMENTS

| | | |
|---|---|---|
| AU | 2003215396 | 9/2003 |
| CH | 522 572 | 6/1972 |

(Continued)

OTHER PUBLICATIONS

Office Action dated Sep. 22, 2011 from U.S. Appl. No. 11/790,779.

(Continued)

*Primary Examiner* — Deborah D Carr
(74) *Attorney, Agent, or Firm* — Nixon & Vanderhye P.C.

(57) ABSTRACT

The subject application relates to methods of treatment of peripheral vascular disease (PVD) as well as ischemic osteonecrosis, peritoneal ischemia, chronic ocular disease, macular degeneration, or diabetic retinopathy, comprising administering a therapeutically effective amount of a trans carotenoid. The invention also relates to the use of such carotenoids as pretreatments for mammals at risk of an ischemic event.

24 Claims, 2 Drawing Sheets

(56) References Cited

U.S. PATENT DOCUMENTS

| | | | |
|---|---|---|---|
| 4,105,855 A | 8/1978 | Schulz et al. | |
| 4,176,179 A | 11/1979 | Gainer | |
| 4,216,211 A | 8/1980 | Francis | |
| 4,727,064 A | 2/1988 | Pitha | |
| 5,032,613 A | 7/1991 | Watson | |
| 5,424,407 A * | 6/1995 | Tanaka et al. | 536/4.1 |
| 5,817,332 A | 10/1998 | Urtti et al. | |
| 6,060,511 A * | 5/2000 | Gainer | 514/558 |
| 6,150,561 A | 11/2000 | Kreienbühl et al. | |
| 7,145,025 B2 | 12/2006 | Lockwood et al. | |
| 7,446,101 B1 | 11/2008 | Madhavi et al. | |
| 2002/0065320 A1 | 5/2002 | Messadek | |
| 2003/0072801 A1 | 4/2003 | Curatolo et al. | |
| 2003/0180282 A1 | 9/2003 | Serebruany et al. | |
| 2003/0186931 A1 | 10/2003 | Matsuo et al. | |
| 2004/0014725 A1 | 1/2004 | Gainer et al. | |
| 2004/0109920 A1 | 6/2004 | Reuscher et al. | |
| 2004/0116729 A1 | 6/2004 | Gainer et al. | |
| 2004/0162329 A1 | 8/2004 | Lockwood et al. | |
| 2005/0113372 A1 | 5/2005 | Lockwood et al. | |
| 2006/0194973 A1 | 8/2006 | Gainer et al. | |
| 2006/0233877 A1 | 10/2006 | Messadek et al. | |
| 2006/0276372 A1 | 12/2006 | Lockwood et al. | |
| 2006/0281724 A1 | 12/2006 | Loria | |
| 2007/0088248 A1 | 4/2007 | Glenn et al. | |
| 2007/0135521 A1 | 6/2007 | Okada | |
| 2007/0166339 A1 | 7/2007 | Gupta | |
| 2008/0113031 A1 | 5/2008 | Moodley et al. | |
| 2008/0255246 A1 | 10/2008 | Gainer | |
| 2009/0110746 A1 | 4/2009 | Gainer et al. | |
| 2009/0118227 A1 | 5/2009 | Jouni et al. | |
| 2009/0169586 A1 | 7/2009 | Tracton | |
| 2009/0176287 A1 | 7/2009 | Schmidt-Dannert et al. | |

FOREIGN PATENT DOCUMENTS

| | | |
|---|---|---|
| CN | 1215723 A | 5/1999 |
| CN | 1708480 A | 12/2005 |
| CN | 1708480 A | 12/2005 |
| CN | 1997365 A | 7/2007 |
| EP | 0 612 815 A1 | 8/1994 |
| EP | 0 908 449 | 4/1999 |
| EP | 1 192 947 A1 | 4/2002 |
| GB | 2 353 934 | 3/2001 |
| JP | 45-014114 | 5/1970 |
| JP | 61-254161 | 11/1986 |
| JP | 63-059831 | 3/1988 |
| JP | 63-59831 | 3/1988 |
| JP | 63-222114 | 9/1988 |
| JP | 63-222114 A | 9/1988 |
| JP | 1-238536 | 9/1989 |
| JP | 2-121934 | 5/1990 |
| JP | 05-032531 | 2/1993 |
| JP | 5-32531 | 2/1993 |
| JP | H-09512552 | 12/1997 |
| JP | 10-502388 T | 3/1998 |
| JP | 11029466 | 2/1999 |
| JP | 11-180901 A | 6/1999 |
| JP | 11-180901 | 7/1999 |
| JP | 2000-007570 | 1/2000 |
| JP | 2001-511135 A | 8/2001 |
| JP | 2002-538113 | 11/2002 |
| JP | 2003-26607 A | 1/2003 |
| JP | 2003-201238 | 7/2003 |
| JP | 2005-53841 | 3/2005 |
| JP | 2006-525270 | 11/2006 |
| JP | 2006-342108 | 12/2006 |
| JP | 2006342108 A | 12/2006 |
| JP | 2007-522076 | 8/2007 |
| JP | 2009-274988 | 5/2010 |
| JP | 2010-110185 | 10/2010 |
| RU | 2107496 | 3/1998 |
| RU | 2226096 C1 | 3/2004 |
| RU | 2256446 | 7/2005 |
| RU | 2265434 C2 | 12/2005 |
| WO | WO 92/15544 | 9/1992 |
| WO | WO 9500130 | 1/1995 |
| WO | WO 98/14183 | 4/1998 |
| WO | WO 98/14183 A1 | 4/1998 |
| WO | WO 9814183 A1 | 4/1998 |
| WO | WO 98/32421 | 7/1998 |
| WO | WO 03/072734 | 9/2003 |
| WO | WO 03/72734 A2 | 9/2003 |
| WO | WO 03/072734 A2 | 9/2003 |
| WO | WO 03/072734 A3 | 9/2003 |
| WO | WO 2004/011423 | 2/2004 |
| WO | WO 2004/049095 | 6/2004 |
| WO | WO 2004049095 | 6/2004 |
| WO | WO 2005/028411 | 3/2005 |
| WO | WO 2005/028411 A1 | 3/2005 |
| WO | WO 2005/120495 | 12/2005 |
| WO | WO 2005120495 | 12/2005 |
| WO | WO 2006/104610 | 10/2006 |
| WO | WO 2006/104610 A2 | 10/2006 |
| WO | WO 2008/014685 A1 | 2/2008 |
| WO | WO 2008/027687 | 3/2008 |
| WO | WO 2008/102563 A1 | 8/2008 |
| WO | WO 2008/135090 A1 | 11/2008 |
| WO | WO 2008/136900 | 11/2008 |
| WO | WO 2009/111688 A2 | 9/2009 |
| WO | WO 2011/152869 A1 | 12/2011 |

OTHER PUBLICATIONS

International Search Report dated Sep. 9, 2011 in PCT/US 11/00997.
Written Opinion dated Sep. 9, 2011 in PCT/US 11/00997.
Mexican Office Action dated Oct. 20, 2011 (with English translation).
Johnson, et al, *Journal of Pharmaceutical Sciences*, vol. 85, No. 7, 1996, pp. 670-679, "Synergistic effects of chemical enhancers and therapeutic ultrasound on transdermal drug delivery."
Eurasian Patent Office Action (English translation) dated Nov. 9, 2011.
Japanese Office Action mailed Oct. 4, 2011, and English translation.
Wenkert, E., et al, J. Org. Chem., vol. 55, No. 25, 1990, pp. 6203-6214, (XP002317164).
Nihon Butsuri Gakkai Shi, *Journal of the Physical Society of Japan*, 1995, 50(7), p. 555-561, "Structure and Function of Cartenoid in Photosynthetic System."
Office Action dated Mar. 16, 2012 from U.S. Appl. No. 13/137,324.
EPO Notice dated Jun. 11, 2012, from European Patent Application No. EP 08742781.1.
Japanese Patent Office Action dated Jul. 10, 2012, from Japanese Patent Application No. 2009-279890 based on PCT/US03/26424, and its English translation.
Helvetica Chemica Acta, 1960, 43(6), p. 1738-1745.
Journal of Organic Chemistry, 1990, 55(25), pp. 6203-6214.
Extended European Search Report dated Nov. 21, 2012 issued by the EPO and Preliminary Opinion.
Lancrajan, I., et al, *Chemistry and Physics of Lipids*, vol. 112, No. 1, Jul. 2001, pp. 1-10, "Carotenoid incorporation into natural membranes from artificial carriers: liposomes and β-cyclodextrins," XP55044152.
Pfitzner, I., et al, *Biochemica et Biophysica Acta*, General Subjects, Elsevier Science Publishers, NL, vol. 1474, No. 2, Apr. 6, 2000, pp. 163-168, "Carotenoid:methyl-β-cyclodextrin formulations: an improved method for supplementation of cultured cells," XP004276552.
Wilkins, E.S., et al, *Cancer Biochem. Biophys*, Gordon and Breach Science Publishers Ltd., vol. 3, 1979, pp. 71-74, "The Effect of Crocetin on the Irradiation of Walker-256: In Vitro and In Vivo Studies," XP008157982.
Rowinsky, E.K., *Oncology*, vol. 10, no. Suppl. 5, Oct. 1999, pp. 61-70, "Novel Radiation Sensitizers Targeting Tissue Hypoxia," XP009044613.
European Patent Office Action dated Oct. 31, 2011, from European Patent Application No. EP 06758166.0.
International Preliminary Report on Patentability (IPRP) (Chapter I) for PCT/US2010/001794, issued Jan. 12, 2012.

(56) References Cited

OTHER PUBLICATIONS

Australian Office Action dated Dec. 23, 2011.
EP Office Action dated Oct. 17, 2011, from European Patent Application No. EP 08742781.1.
International Preliminary Report on Patentability (IPRP) (Chapter I) for PCT/US2011/000997, issued Dec. 13, 2012.
Eurasian Patent Office Action (and English translation) dated Nov. 17, 2011.
General Information on Perfluorane. Medline.ru-Biomeditsinskii Zhurnal, 2004, vol. 5, art. 16, pp. 68-69, www.medline.ru/public/art/tom5/art8-perf2.phtm (with English translation).
Abusuev, A.A., Clinical Course of Myocardial Infarction in Treatment with Perfluorane, in Perfluorocarbon Compounds in Experimental and Clinical Medicine, Collected Works of the Russian Scientific Conference, St. Petersburg, 2004, p. 12.
Kichev, G.S., et al, Experience of Using Perfluorane in Treating Critical Conditions of Various Geneses. Medline.ru-Biomeditsinskii Zhurnal, 2004, vol. 5, art. 53, pp. 175-177.
Burukhina, A.N., et al, Experience of Using Perfluorane in Treating Acute Massive Hemorrhage in Obstetric Practice, in Collected Works of the 12th Scientific and Practical Conference of Physicians "Topical Issues in Modern Medicine," Novosibirsk, 2002, Chapter 2, pp. 39-40.
Borisova, I.V., et al, Renal and Neuroprotective Effects of Perfluorane in Induced Toxic Renal Injury in Rats. Medline.ru-Biomeditsinskii Zhkurnal, 2004, vol. 5, art. 16, pp. 136-139.
Chinese Patent Office Action dated May 3, 2012, from Chinese Patent Application No. 03804566.4 based on PCT/US03/05521, and its English translation.
Ladig et al, *J. Am. Chem. Soc.*, 120, 9394-9395 (1998).
Office Action dated May 10, 2012 from U.S. Appl. No. 13/067,469.
Lang et al, Parkinson's Disease, New England Journal of Medicine, vol. 339, No. 15, 1044-1053 (1998).
Chinese Patent Office Action dated Jun. 6, 2012, from Chinese Patent Application No. 200880015671.8 based on PCT/US08/004708, and its English translation.
Mexican Patent Office Action dated Aug. 27, 2012 that corresponds to Applicant's U.S. Appl. No. 12/081,236, filed Apr. 11, 2008. [no translation].
Zheng, S., et al, J. Cardiovasc. Pharmacol, vol. 47, No. 1, Jan. 2006, pp. 70-76, "Crocetin Attenuates Atherosclerosis in Hyperlipidemic Rabbits Through Inhibition of LDL Oxidation." XP009135396.
English translation of Japanese Office Action dated Jul. 10, 2012, for applicant's Japanese Patent Application No. 2009-274988 corresponding to PCT/US03/05521 filed Feb. 25, 2003.
Office Action dated Sep. 18, 2012 from U.S. Appl. No. 13/137,337.
Korean Patent Office Action dated Sep. 26, 2012, from Korean Patent Application No. 10-2007-7021197 based on PCT/US2006/006422, and its English translation.
Supplementary European Search Report dated Oct. 29, 2012 issued by the EPO and Preliminary Opinion.
Lapchak, Paul A., *Brain Research*, vol. 1309, Jan. 14, 2010, pp. 136-145, "Efficacy and safety profile of the carotenoid trans sodium crocetinate administered to rabbits following multiple infarct ischemic strokes: A combination therapy study with tissue plasminogen activator," XP-002686117.
Wang, Y, et al, Society for Neuroscience Abstract Viewer and Itinerary Planner, vol. 38, 2008, "The effect of trans-sodium crocetinate in a model of intracranial hemorrhage," XP009163975.
English translation of Chinese Patent Office Action issued on Jan. 18, 2012 in Chinese Patent Application No. 200680013663.0 based on PCT/US2006/06422.
Office Action dated Jan. 15, 2013 from U.S. Appl. No. 13/067,469.
Chinese Office Action issued Jun. 14, 2012, from Chinese Patent Application No. 200880114310.9 that corresponds to PCT/US2008/012440, and its English translation.
Office Action dated Jul. 26, 2012 from U.S. Appl. No. 12/801,726.
European Office Action dated Apr. 25, 2012.

Moelbert, S., et al, Biophysical Chemistry 112, No. 1, (2004) pp. 45-57, "Kosmotropes and chaotropes: modeling preferential exclusion, binding and aggregate stability," XP004610642.
Finney, J., et al, Annals of the New York Academy of Sciences, vol. 141, No. 1, Mar. 15, 1967, pp. 231-241, "Protection of the ischemic heart with DMSO alone or DMSO with hydrogen peroxide."
Japanese Office Action dated Jul. 10, 2012, for applicant's Japanese Patent Application No. 2009-274988 corresponding to PCT/US03/05521 filed Feb. 25, 2003, and its English translation.
R. Wirz et al, Helv. Chim. Acta, vol. 43, No. 6, 1738-1745 (1960), XP008042762.
E. Wenkert et al, J. Org. Chem., vol. 55, No. 25, 6203-6214 (1990), XP-002317164.
Japanese Patent Office Action dated Feb. 19, 2013, from applicant's Japanese Patent Application No. 2009-279890 corresponding to PCT/US03/26424 filed Aug. 25, 2003, and its English translation.
Canadian Office Action dated Mar. 26, 2013, for applicant's Canadian Patent Application No. 2,598,882 corresponding to PCT/US06/006422 filed Feb. 24, 2006.
Chinese Patent Office Decision of Rejection dated May 2, 2013 and its English translation, corresponding to PCT/US2006/06422 filed on Feb. 24, 2006.
Laidig, K.E. et al, Altering Diffusivity in Biological Solutions through Modification of Solution Structure and Dynamics, *Journal of the American Chemical Society*, 1998, vol. 120, No. 36, pp. 9394-9395, (XP 002970835).
Office Action dated Jun. 12, 2013 from U.S. Appl. No. 12/801,726.
Israel Office Action dated Apr. 10, 2013, from applicant's Israel Patent Application No. 185460 corresponding to PCT/US06/06422 filed Feb. 24, 2006, and its English translation.
Japanese Office Action (Notice of Reasons for Rejection) dated Jun. 4, 2013, from applicant's Japanese Patent Application No. 2011-209754 corresponding to PCT/US06/06422 filed Feb. 24, 2006, and its English translation.
Pharmacia, 1991, vol. 27, No. 7, pp. 703-705 (no English translation).
Canadian Office Action dated May 30, 2013, for applicant's Canadian Patent Application No. 2,683,760 corresponding to PCT/US2008/004708 filed Apr. 11, 2008.
Japanese Decision of Rejection dated May 21, 2013, from applicant's Japanese Patent Application No. 2010-110185 corresponding to PCT/US2003/05521 filed Feb. 25, 2003, and its English translation.
Chinese Office Action issued May 6, 2013, from Chinese Patent Application No. 201080027664.7 that corresponds to PCT/US2010/001794, and its English translation.
Chinese Search Report dated Mar. 18, 2013, and its English translation.
Chinese Office Action issued Jul. 9, 2013, from Chinese Patent Application No. 200880114310.9 that corresponds to PCT/US2008/012440, and its English translation.
Chinese Search Report dated Jun. 27, 2013, and its English translation.
Chinese Office Action issued Jan. 28, 2013, from Chinese Patent Application No. 200880015671.8 that corresponds to PCT/US2008/004708, and its English translation.
India Office Action (Examination Report) dated Feb. 21, 2013, for applicant's India Patent Application No. 6688/DELNP/2007 corresponding to PCT/US2006/006422 filed Feb. 24, 2006.
Schwieter, U., et al, "Synthesen in der Carotinoid-Reiche 20. Mitteilung Neu Synthesen von Apocarotinoiden," Helvetica Chimica Acta, vol. 1, (1966), pp. 369-390, compound 36 on p. 375, XP-002575142.
Database HCAPLUS on STN, DN 141:388250, Magesh, V. "Studies on the anti-tumor effect of crocetin against benzo(a)pyrene induced lung cancer in Swiss albino mice." XP008117254 Retrieved from STN Databse accession No. (141:388250) & Biomedicine, (Chennai, India) (2003), 23 (3 & 4), 96-99, Abstract.
Office Action dated Jul. 16, 2013 from U.S. Appl. No. 13/137,324.
Extended European Search Report dated Mar. 28, 2013 issued by the EPO and Written Opinion.
Zheng, S., et al, Journal of Cardiovascular Pharmacology, vol. 47, No. 1, Jan. 2006, pp. 70-76, "Crocetin Attenuates Atherosclerosis in Hyperlipidemic Rabbits Through Inhibition of LDL Oxidation." XP009135396.

(56) References Cited

OTHER PUBLICATIONS

New Zealand Examination Report dated Oct. 2011 that issued in the applicant's New Zealand Patent Application No. 595624.
Examination Report dated Apr. 7, 2010 issued by the New Zealand Patent Office in Applicants' corresponding foreign application No. 584433.
Wirz, R., et al, Helv. Chim. Acta, vol. 43, No. 6, 1960, pp. 1738-1745, (XP008042762).
Isler, O., et al, Helv. Chim. Acta, vol. 40, No. 5, 1957, pp. 1242-1249, (XP008042920).
Database Caplus, Chemical Abstracts Service, Columbus, Ohio, US; (XP002317165) [JP 63 059831].
Wenkert, E., et al, J. Org. Chem., vol. 55, No. 25, 1990, p. 6203-6214 (XP002317164).
Database Caplus, Chemical Abstracts Service, Columbus, Ohio, US; (XP002317166) [JP 05 032531].
Gibson, T.W., et al, J. Org. Chem., vol. 41, No. 5, 1976, pp. 791-793, (XP002325593).
Japanese Office Action dated Apr. 22, 2014 from applicant's Japanese Application No. P2010-531078 corresponding to PCT/US08/012440 filed Oct. 31, 2008, and its English translation.
Japanese Office Action (Final Rejection) dated Sep. 10, 2013, from applicant's Japanese Application No. P2009-279890 corresponding to PCT/US03/26424 filed Aug. 25, 2003, and its English translation.
English Translation of Israel Office Action dated May 4, 2014 from applicant's Israel Patent Application No. 185460 corresponding to PCT/US06/06422 filed Feb. 24, 2006.
U.S. Office Action dated Jun. 5, 2014 from U.S. Appl. No. 13/067,469, Gainer.
U.S. Office Action dated Jun. 9, 2014 from U.S. Appl. No. 13/137,324, Gainer et al.
Japanese Office Action (Final Rejection) dated Nov. 26, 2013, from applicant's Japanese Application No. P2010-503069 corresponding to PCT/US08/004708 filed Apr. 11, 2008, and its Enslish translation.
Chinese Office Action issued Mar. 19, 2014, from Chinese Patent Application No. 200880015671.8 that corresponds to PCT/US2008/004708, and its English translation.
U.S. Office Action dated Jan. 30, 2014 from U.S. Appl. No. 12/801,726, Gainer.
Japanese Office Action (Final Rejection) dated Feb. 4, 2014 from applicant's Japanese Application No. P2011-209754 corresponding to PCT/US06/06422 filed Feb. 24, 2006, and its English translation.
Pharmacia. 1991, vol. 27, No. 7, pp. 703-705.
U.S. Office Action dated May 8, 2014 from U.S. Appl. No. 13/507,365, Gainer.
EP Office Action dated Mar. 12, 2014, from applicant's European Patent Application No. EP 12166293.6, corresponding to PCT/US2006/006422 filed Feb. 24, 2006.
Lancrajan, Ioana, et al, Chemistry and Physics of Lipids, vol. 112, No. 1, (2001), pp. 1-10, "Carotenoid incorporation into natural membranes from artificial carriers: liposomes and beta-cyclodextrins," XP55044152.
Pfitzner, Inka, et al, Biochemica et Biophysica Acta, vol. 1474, No. 2, (2000), pp. 163-168, "Carotenoid:methyl-beta-cyclodextrin formulations: an improved method for supplementation of cultured cells," XP004276552.
Wilkins, E.S., et al, Cancer Biochem. Biophys., vol. 3, (1979), pp. 71-74, "The Effect of Crocetin on the Irradiation of Walker-256: in vitro and in vivo studies," XP008157982.
Rowinsky, Eric K., Oncology, vol. 13, No. 10, Supplement No. 5, (Oct. 1999), pp. 61-70, "Novel Radiation Sensitizers targeting Tissue Hypoxia," XP009044613.
Chinese Office Action issued Mar. 31, 2014, from Chinese Patent Application No. 201210063676.6 that corresponds to PCT/US2003/026524, filed Aug. 25, 2003, and its English translation.
Chinese Search Report dated Mar. 19, 2014 from Chinese Patent Application No. 201210063676.6 that corresponds to PCT/US2003/026524, filed Aug. 25, 2003, and its English translation.

Wenkert, E., et al, J. Org. Chem., vol. 55, No. 25, 1990, pp. 6203-6214 "Polyene Synthesis. Ready Construction of Retinol-Carotene Fragments . . . Corticrocin." (XP002317164).
Ladig, K.E., et al, J. Am Chem. Soc., vol. 120, pp. 9394-9395 (1998) "Altering Diffusivity in Biological Solutions through Modification of Solution Structure and Dynamics."
Office Action dated Jul. 29, 2013 from U.S. Appl. No. 13/067,469.
Lang et al, Parkinson's Disease, New England Journal of Medicine, vol. 339, No. 15, pp. 1044-1053 (1998).
Office Action dated Aug. 22, 2013 from U.S. Appl. No. 13/507,365.
Gainer, John L., "Trans-Sodium Crocetinate for Treating Hypoxia/Ischemia," Expert Opinion on Investigational Drugs, vol. 17, No. 6, 2008, pp. 917-924.
Wang, Y. et al., "The Effect of Trans-Sodium Crocetinate in a Model of Intracranial Hemorrhage," Society for Neuroscience Abstract Viewer and Itinerary Planner, vol. 38, 2008, 2 pp.
Japanese Office Action dated Jun. 24, 2014 issued in Japanese Patent Application No. P2012-516071 and English Translation, 10 pp.
U.S. Office Action dated Jun. 26, 2014 issued in U.S. Appl. No. 13/137,337, 24 pp.
U.S. Office Action dated Nov. 20, 2013 from U.S. Appl. No. 13/137,337, Gainer et al.
Supplementary (Extended) European Search Report dated Oct. 21, 2013 in European Patent Application No. EP11790107.4 issued from PCT/US2011/000997 filed on Jun. 2, 2011, together with the Opinion.
Lapchak, P.A., Brain Research, vol. 1309, Jan. 2010, pp. 136-145, "Efficacy and safety profile of the carotenoid trans sodium crocetinate administered to rabbits following multiple infarct ischemic strokes: A combination therapy study with tissue plasminogen activator," XP-002686117.
Wang, Y., et al, Abstracts of the Annual Meeting of the Society for Neuroscience, Society for Neuroscience, Washington, DC, US, vol. 38, Nov. 15, 2008, "The effect of trans-sodium crocetinate in a modes of intracranial hemorrhage," XP-009163975.
Gainer, J.L., et al, Pulmonary Pharmacology & Therapeutics, Academic Press, GB, vol. 18, No. 3, Jun. 1, 2005, pp. 213-216, "The effects of trans sodium crocetinate (TSC) in a rat oleic acid model of acute lung injury," XP004737366.
Japanese Office Action (Reasons for Rejection) dated Jun. 18, 2013, in Japanese App. No. 2010-531078 (no English translation).
Chinese Office Action dated Jul. 21, 2014 issued in Chinese Patent Application No. 200680013663.0 and English Translation, 9 pp.
Chinese Office Action dated Jul. 24, 2014 issued in Chinese Patent Application No. 200880114310.9 and English Translation, 19 pp.
Chinese Office Action dated Aug. 15, 2014 issued in Chinese Patent Application No. 201080027664.7 and English Translation, 13 pp.
Helvetica Chimica Acta, vol. 43 (6), 1960, pp. 1738-1745.
Japanese Office Action mailed Sep. 9, 2014 issued in Japanese Patent Application No. 2013-197629, 5 pp.
Journal of Organic Chemistry, vol. 55 (25), Dec. 7, 1990, pp. 6203-6214.
Korean Office Action dated Jul. 28, 2014 issued in Korean Patent Application No. Oct. 2009-7023432 and English Translation, 8 pp.
Galinski, Erwin A. et al., "The Kosmotropic (Structure-Forming) Effect of Compensatory Solutes," Comp. Biochem. Physiol., vol. 117A, No. 3, Dec. 31, 1997, pp. 357-365.
Laidig, Keith E. et al., "Altering Diffusivity in Biological Solutions through Modification of Solution Structure and Dynamics," Journal of the American Chemical Society, vol. 120, No. 36, pp. 9394-9395.
Lever, M. et al., "Some Ways of Looking at Compensatoroy Kosmotropes and Different Water Environments," Comparative Biochemistry and Physiology Part A, vol. 130, Dec. 31, 2001, pp. 471-486.
Stennett, Amanda K. et al., "trans-Sodium Crocetinate and Diffusion Enhancement," The Journal of Physical Chemistry B Letters, vol. 110, Issue 37, Aug. 29, 2006, pp. 18078-18080.
Tong, Linhui, "Cyclodextrins Chemistry: Fundamentals and Application," Science Press, Mar. 2001, pp. 360-364.
United States Office Action dated Sep. 8, 2014 issued in U.S. Appl. No. 12/801,726, 23 pp.

* cited by examiner

USE OF BIPOLAR TRANS CAROTENOIDS AS A PRETREATMENT AND IN THE TREATMENT OF PERIPHERAL VASCULAR DISEASE

This application is a divisional from U.S. patent application Ser. No. 12/081,236, filed Apr. 11, 2008, the entire contents of which are hereby incorporated by reference, and which claims the benefit of U.S. Provisional Application No. 60/907,718, filed Apr. 13, 2007, the entire contents of which are hereby incorporated by reference in this application.

The subject application relates to the treatment of peripheral vascular disease and pretreatments with bipolar trans carotenoids.

BACKGROUND OF THE INVENTION

There are many disorders characterized by circulatory system problems:

Peripheral Vascular Disease

The circulatory system consists of two types of blood vessels, arteries and veins, which carry the blood throughout the body. Arteries carry oxygen- and nutrient-rich blood from the heart to the organs and cells. Among both arteries and veins, central blood vessels are those leading directly to or from the heart, and peripheral blood vessels are those in the feet, legs, lower abdomen, arms, neck or head. Veins carry oxygen-depleted blood and wastes through the kidneys, liver, and lungs, where wastes are filtered out and removed from the body. The venous blood is then again filled with oxygen in the lungs and returned back to the heart. The two types of blood vessels are interconnected by small web-like vessels called capillaries.

The term peripheral vascular disease (PVD) refers to damage, dysfunction or obstruction within peripheral arteries and veins. Peripheral artery disease (PAD) is the most common form of PVD.

Peripheral vascular disease is the most common disease of the arteries and is a very common condition in the United States. It occurs mostly in people older than 50 years. Peripheral vascular disease is a leading cause of disability among people older than 50 years, as well as in those people with diabetes.

About 10 million people in the United States have peripheral vascular disease, which translates to about 5% of people older than 50 years. The number of people with the condition is expected to grow as the population ages. Men are slightly more likely than women to have peripheral vascular disease.

There are two types of peripheral vascular disease. The first type is peripheral arterial disease (PAD), which refers to diseased peripheral arteries. Peripheral artery disease is often named after the artery that is affected.

Carotid artery disease. Narrowing of one or more carotid arteries in the neck, which supply oxygen-rich blood to the brain, through atherosclerosis.

PAD of the lower extremities (legs). Narrowing of one or more arteries in the leg (usually the femoral artery near the groin).

PAD of the renal arteries. Narrowing of one or more renal arteries, leading to the kidneys.

Abdominal aortic aneurysm (AAA). The bulging or ballooning out of part of the wall of the abdominal section of the aorta, the body's main artery that carries oxygen-rich blood from the heart to the body.

Raynaud's phenomenon is a condition that affects the blood vessels in the extremities—generally, the fingers and toes. It is characterized by episodic attacks, called vasospastic attacks, in which the blood vessels in the digits (fingers and toes) constrict (narrow), usually in response to cold temperatures and/or emotional stress. When this condition occurs on its own, it is called primary Raynaud's phenomenon. When it occurs with another condition such as scleroderma or lupus, it is called secondary Raynaud's phenomenon.

Buerger disease. A rare type of peripheral arterial disease that involves inflammation of the smaller arteries in the extremities and gets worse over time, causing increasing pain in the legs (claudication). Buerger's disease, also called thromboangitis obliterans, is a rare disease of the arteries and veins in the arms and legs. Buerger's disease is characterized by a combination of inflammation and clots in the blood vessels, which impairs blood flow. This eventually damages or destroys tissues and may lead to infection and gangrene. Buerger's disease usually begins in the hands and feet and may progress to affect larger areas of the limbs.

Polyarteritis nodosa (PN). A rare and potentially deadly form of vasculitis, a condition in which small to medium-sized blood vessels (usually arteries) are abnormally inflamed. PN causes structural damage to the inside walls of the inflamed blood vessels, which reduces the flow of blood.

The second type of peripheral vascular disease is peripheral venous disorders, which refer to problems in the peripheral veins. There are a number of different peripheral venous disorders, which include:

Phlebitis. Inflammation of the vein.

Thrombophlebitis (including superficial vein thrombosis and deep vein thrombosis). An obstructing blood clot (a thrombus) has formed, causing the surrounding veins to become inflamed (phlebitis).

Varicose veins. Abnormally widened veins that are swollen, dark and frequently twisted or contorted instead of straight. They usually occur in the legs and may cause swelling (edema), inflammation and a dark color around the ankles.

Chronic venous insufficiency. An advanced stage of leg vein disease in which the veins become incompetent, causing blood to pool in the legs and feet, and sometimes to leak backwards.

The most common cause of peripheral vascular disease is atherosclerosis. Atherosclerosis is a gradual process in which a material called plaque builds up inside the arteries. This material is a mixture of lipids, calcium, scar tissues, and other substances which harden slightly, forming the plaques (sometimes called lesions). Atherosclerosis is frequently called arteriosclerosis, or just plain "hardening of the arteries." Atherosclerosis can reduce blood flow, in particular, it can reduce blood flow to various parts of the body including the extremities, the heart, or to the brain. Once the atherosclerotic plaques form, they block, narrow, or weaken the vessel walls.

When an artery is blocked or narrowed, the part of the body supplied by that artery does not get enough blood/oxygen. The lack of blood flow in the extremities such as the leg or foot can be detected by measuring the blood pressure in several places. An ankle/brachial index has been defined as a way to classify this type of blood flow. The ankle/brachial index (ABI) is the ratio of the blood pressure at the ankle to that in the upper arm. A value greater than or equal to 1.0 of the ABI suggests that blood flow is normal in the limbs, and a value less than 1.0 suggests otherwise (diabetics with PVD can have ABI values of greater than 1). A lack of blood flow to the extremities then leads to a lack of oxygen getting to the tissues, and this is known as ischemia.

PVD can be due to other causes besides atherosclerosis. These include the following:

Blood clot: A blood clot can block a blood vessel (thrombus/embolus).

Diabetes: One of the complications of diabetes is PVD.

Inflammation of the arteries: This condition is called arteritis and can cause narrowing or weakening of the arteries.

Infection: The inflammation and scarring caused by infection can block, narrow, or weaken blood vessels. Both salmonellosis (infection with *Salmonella* bacteria) and syphilis are two infections traditionally known to infect and damage blood vessels.

Structural defects: Defects in the structure of a blood vessel can cause narrowing. Most of these cases are acquired at birth. Takayasu disease is a vascular disease affecting the upper vessels of the body and affects usually Asian females.

Injury: Blood vessels can be injured in an accident such as a car wreck or a bad fall.

Only about one-half of the individuals with peripheral vascular disease have symptoms. Almost always, symptoms are caused by the leg muscles not getting enough blood. Whether there are symptoms depends partly on which artery is affected and to what extent blood flow is restricted.

The most common symptom of peripheral vascular disease in the legs is pain in one or both calves, thighs, or hips. The pain usually occurs while walking or climbing stairs and stops during rest. Such a pain is called intermittent claudication. It is usually a dull, cramping pain. It may also feel like a heaviness, tightness, or tiredness in the muscles of the legs.

Cramps in the legs have several causes, but cramps that start with exercise and stop with rest most likely are due to intermittent claudication. When the blood vessels in the legs become even more blocked, leg pain at night is very typical, and the individual almost always hangs his or her feet down to ease the pain. Hanging the legs down allows for blood to passively flow into the distal part of the legs.

Other symptoms of peripheral vascular disease include the following:

Buttock pain

Numbness, tingling, or weakness in the legs

Burning or aching pain in the feet or toes while resting

A sore on a leg or a foot that will not heal

One or both legs or feet feel cold or change color (pale, bluish, dark reddish)

Loss of hair on the legs

Impotence

Having symptoms while at rest is a sign of more severe disease.

A therapy currently used to treat the ischemia of PVD is to have the patient breathe enriched oxygen, frequently under pressure such as in hyperbaric oxygen therapy (HBOT). One method for doing this employs 100% oxygen at 1.3-1.4 atmospheres pressure.

Coronary Artery Disease

Coronary artery disease (CAD) occurs when the arteries that supply blood to the heart muscle (the coronary arteries) become narrowed. The arteries narrow due to buildup of a material called plaque from atherosclerosis on their inner walls. As the plaque increases, the insides of the coronary arteries get narrower and less blood can flow through them. Eventually, blood flow to the heart muscle is reduced, and, because blood carries much-needed oxygen, the heart muscle is not able to receive the amount of oxygen it needs. Reduced or cutoff blood flow and oxygen supply to the heart muscle can result in:

Angina. Angina is chest pain or discomfort that occurs when the heart does not get enough blood.

Heart attack. A heart attack happens when a blood clot develops at the site of plaque in a coronary artery and suddenly cuts off most or all blood supply to that part of the heart muscle. Cells in the heart muscle begin to die if they do not receive enough oxygen-rich blood. This can cause permanent damage to the heart muscle.

Over time, CAD can weaken the heart muscle and contribute to:

Heart failure. In heart failure, the heart can't pump blood effectively to the rest of the body. Heart failure does not mean that the heart has stopped or is about to stop. Instead, it means that the heart is failing to pump blood the way that it should.

Arrhythmias. Arrhythmias are changes in the normal beating rhythm of the heart. Some can be quite serious.

CAD is the most common type of heart disease. It is the leading cause of death in the United States in both men and women.

Embolism

Blood flow decreases due to a thrombus or embolism. An embolism occurs when an object (the embolus, plural emboli) migrates from one part of the body (through circulation) and cause(s) a blockage (occlusion) of a blood vessel in another part of the body. This can be contrasted with a "thrombus" which is the formation of a clot within a blood vessel, rather than being carried from somewhere else.

Blood clots form the most common embolic material by far: other possible embolic materials include fat globules (a fat embolism), air bubbles (an air embolism), talc embolism (often following drug abuse), septic emboli (containing pus and bacteria), atherosclerotic emboli, or amniotic fluid. Emboli often have more serious consequences when they occur in the so-called "end-circulation" areas of the body that have no redundant blood supply, such as the brain, heart, and lungs.

Assuming a normal circulation, a thrombus or other embolus formed in a systemic vein frequently impact in the lungs, after passing through the right side of the heart. This forms a pulmonary embolism that can be a complication of deep-vein thrombosis.

Some congenital abnormalities of the circulation, especially septal defects (holes in the cardiac septum), allow an embolus from a systemic vein to cross into the arterial system and land anywhere in the body. The most common such abnormality is patent foramen ovale, occurring in about 25% of the adult population, but here the defect functions as a valve which is normally closed, because pressure is slightly higher in the left side of the heart. In unfortunate circumstances, e.g. if patient is coughing just when an embolus is passing, passage to the arterial system may occur.

Emboli starting in the heart (from a thrombus in the left atrium secondary to atrial fibrillation or septic emboli from endocarditis) can cause emboli in any part of the body. An embolus landing in the brain from either the heart or a cerebral artery will likely cause an ischemic stroke.

Embolism of cardiac origin is also frequently encountered in clinical practice. Thrombus formation within the atrium in valvular disease occurs mainly in patients with mitral valve disease, and especially in those with mitral valve stenosis with atrial fibrillation (AF). In the absence of AF, pure mitral regurgitation has low incidence of thromboembolism. Absolute risk of emboli in idiopathic AF depends on other risk factors such as increasing age, hypertension, diabetes, recent heart failure, or previous stroke. Thrombus formation can also take place within the ventricles, and it occurs in approximately 30% of anterior wall myocardial infarctions, compared to only 5% of inferior ones. Other risk factors include poor ejection fraction (<35%), size of infarct, as well as presence of AF. In the first three months after infarction, left ventricle aneurysms have 10% risk of embolization. Patients with prosthetic valves also carry a significant increase in risk of thromboembolism. Risk varies on the valve type (bioprosthetic or mechanical), the position (mitral or aortic), and presence of other factors such as AF, left ventricular dysfunction, previous emboli, etc.

Brain Ischemia

A stroke is associated with a reduced blood flow in the brain. A stroke can be caused by either a clot or a ruptured blood vessel in the brain.

Neurological researchers have been searching for a way to prevent ischemic injury to a brain that is exposed to a lowered oxygen situation. In addition, a primary complication of many types of invasive surgery is hypoxic cell injury (ie., injury to cells due to periods of low oxygen). Common surgical procedures, such as those involving vascular clamping and/or manipulation of cardiac function, entail substantial risk for such injury. The risk of tissue damage resulting from low oxygen is greatest in the nervous system, where the metabolic demands of neurons are extremely high. For example, after coronary artery bypass surgery, some form of cognitive deficit has been reported to occur in many patients.

A transient ischemic attack (TIA) is a "mini-stroke" caused by temporary disturbance of blood supply to an area of the brain, which results in a sudden, brief decrease in brain function. In a TIA, the blood supply is only temporarily blocked. For example, a blood clot may dissolve and allow blood to flow normally again. A TIA is different than a small stroke. The symptoms of TIAs go away in less than 24 hours, usually less than one hour. TIAs do not show lasting changes on CT or MRI scans. Small strokes do show changes on such tests.

In general, therapeutic strategies targeting ischemic injury can be classified by when they are administered: preischemic, intraischemic, and postischemic. A preischemic therapeutic intervention can be thought of as inducing tolerance in the tissues. Such an intervention can also be thought of as providing protection, such as neuroprotection for the brain. Such therapy is sometimes given just prior to an ischemic or hypoxic challenge, but it can also be given earlier than that. If a conditioning stimulus is given several days prior to the injury, it can induce what is called "delayed tolerance" (or "late tolerance"). Some stimuli known to do this are hypoxia, hypothermia, long-term hyperbaric oxygen, and cytokines, among others.

One way to test whether or not a pretreatment therapy induces tolerance or protection in brain tissue is to conduct stroke research. In this research, vessels are tied off so that blood flow to the brain of the animals is greatly reduced, and this induces a stroke. The region of the brain affected by the stroke consists of the ischemic core and the surrounding affected tissue (called the penumbra). By measuring the volumes of those regions it is possible to evaluate the effectiveness of a therapy in inducing tolerance in the brain.

Ischemic Osteonecrosis

Ischemic osteonecrosis means, literally, "dead bone from poor blood flow." It may have either dead bone or bone marrow that has been slowly strangulated or nutrient-starved. Bone with chronically poor blood flow develops either a fibrous marrow (fibers can live in nutrient starved areas), a greasy, dead fatty marrow ("wet rot"), a very dry, sometimes leathery marrow ("dry rot"), or a completely hollow marrow space ("cavitation"). Any bone can be affected, but the hips, knees and jaws are most often involved. Pain is often severe but about ⅓ of patients do not experience pain.

Chronic Ocular Disease

Reduced capillary blood flow may be of consequence in the progression of chronic ocular diseases such as glaucoma.

Macular Degeneration

Macular degeneration, often called AMD or ARMD (age-related macular degeneration), is the leading cause of vision loss and blindness in Americans aged 65 and older. Because older people represent an increasingly larger percentage of the general population, vision loss associated with AMD is a growing problem.

AMD occurs with degeneration of the macula, which is the part of the retina responsible for the sharp, central vision needed to read or drive. Because the macula primarily is affected in AMD, central vision loss may occur. The disease is marked by new blood vessels growing into the eyes.

Diabetic Retinopathy

Diabetic retinopathy is a potentially blinding complication of diabetes that damages the eye's retina. It affects half of all Americans diagnosed with diabetes. Diabetic retinopathy occurs when diabetes damages the tiny blood vessels in the retina. Some people with diabetic retinopathy develop a condition called macular edema. As the disease progresses, it enters its advanced, or proliferative, stage. Fragile, new blood vessels grow along the retina and in the clear, gel-like vitreous humor that fills the inside of the eye. Without timely treatment, these new blood vessels can bleed, cloud vision, and destroy the retina.

Carotenoids are a class of hydrocarbons consisting of isoprenoid units joined in such a manner that their arrangement is reversed at the center of the molecule. The backbone of the molecule consists of conjugated carbon-carbon double and single bonds, and can also have pendant groups.

Crocetin has been shown to cause a reduction in atherosclerotic plaque formation over time in rabbits (Gainer, J. L. and Chisolm, G. M., Oxygen diffusion and atherosclerosis. Atherosclerosis, 19: 135-138, 1974).

U.S. Pat. No. 6,060,511 relates to trans sodium crocetinate (TSC) and its uses. The patent covers various uses of the TSC such as improving oxygen diffusivity and treatment of hemorrhagic shock.

U.S. patent application Ser. No. 10/647,132 relates to synthesis methods for making bipolar trans carotenoid salts (BTC) and methods of using them.

U.S. patent application Ser. No. 11/361,054 relates to improved BTC synthesis methods and novel uses of the BTC.

U.S. Provisional Patent application Ser. No. 61/001,095 relates to a class of therapeutics that enhance small molecule diffusion.

SUMMARY OF THE INVENTION

The subject invention relates to a method of treating a mammal having peripheral vascular disease (PVD) comprising administering a therapeutically effective amount of a trans carotenoid. The invention also relates to a method of reducing the formation of atherosclerotic plaque in a mammal having atherosclerotic plaque comprising administering to said mammal a therapeutically effective amount of a bipolar trans carotenoid. Also disclosed is a method of preventing or reducing damage due to an ischemic event in a mammal at risk of an ischemic event comprising administering to said mammal a therapeutically effective amount of a trans carotenoid. Other embodiments of the invention include methods of treating ischemic osteonecrosis or peritoneal ischemia and of treating chronic ocular disease, macular degeneration, or diabetic retinopathy comprising administering a therapeutically effective amount of a trans carotenoid.

DETAILED DESCRIPTION OF THE INVENTION

Figure 1:
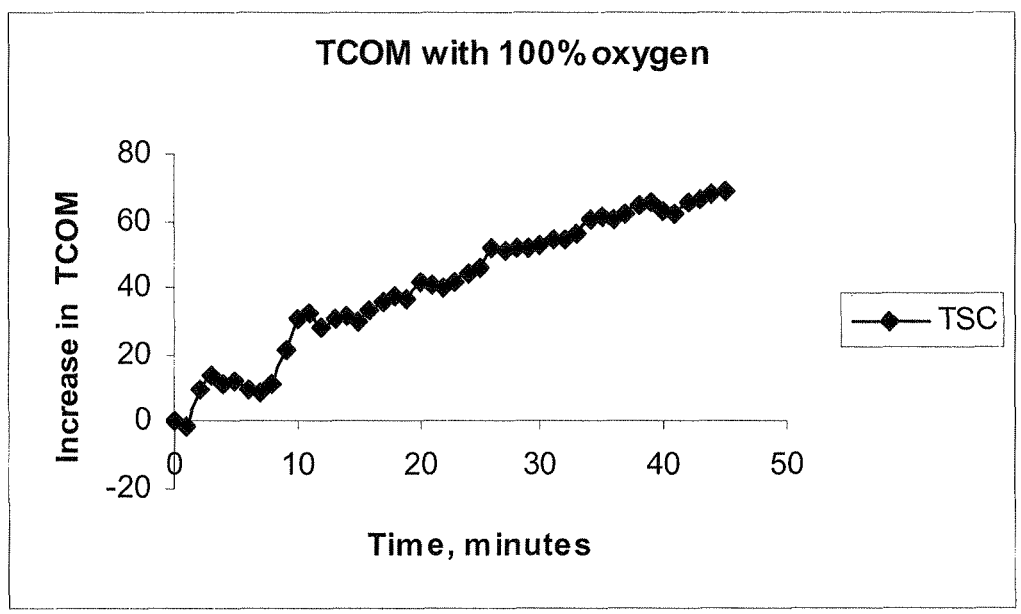
FIG. 1 is a graph of TCOM with 100% oxygen.

The subject application relates to the treatment of peripheral vascular disease with bipolar trans carotenoids, and the use of these compounds as a pretreatment.

Commonly owned U.S. patent application Ser. No. 10/647,132, hereby incorporated by reference in its entirety, relates to synthesis methods for making bipolar trans carotenoid salts (BTC) and methods of using them. Commonly owned U.S. patent application Ser. No. 11/361,054, hereby incorporated by reference in its entirety, relates to improved BTC synthesis methods and novel uses of BTC. Commonly owned U.S. Provisional Patent application Ser. No. 61/001,095, hereby incorporated by reference in its entirety, relates to a class of therapeutics that enhance small molecule diffusion. In one embodiment, the compounds of U.S. Provisional Patent application Ser. No. 61/001,095 can be used as an alternative to the bipolar trans carotenoids discussed herein.

Treatment of Peripheral Vascular Disease with a Bipolar Trans Carotenoid

Administration of a bipolar trans carotenoid (such as TSC) is a beneficial treatment for PVD or any of its symptoms such as claudication and rest pain, both in the short and long terms.

One measurement method for detecting PVD suggested in the literature is with the use of a transcutaneous oxygen electrode (TCOM) on the leg or foot. With PVD, the TCOM readings are lower than in normal individuals. 100% oxygen will cause the TCOM readings to increase. As shown in Example 1, TSC causes the TCOM readings to increase under certain conditions. This is accentuated when the mammal is breathing 100% oxygen or if the mammal is initially hypoxic.

Short Term Treatment

A consequence of PVD is that less oxygen reaches the tissues because there is less blood flow getting to the extremities. Administration of a bipolar trans carotenoid will provide short-term treatment for PVD in that tissues and organs will not be subjected to low oxygen conditions during the treatment periods.

A bipolar trans carotenoid such as TSC can be administered by injection (intravenous or intramuscular) or infusion, or by pulmonary, oral or transdermal routes for hours or days (e.g. 1-4 days). For a dose to be "therapeutically effective" it must have the desired effect, i.e. in the case of PVD, that amount which reduces symptoms (e.g. claudication) and/or increases the level of oxygen in the peripheral arteries and veins. A typical dose is from 0.05 to 5.0 mg/kg in humans, advantageously from 0.1 to 3.5 mg/kg.

A bipolar trans carotenoid can be combined with the oxygen treatment and cause even more oxygen to reach the tissues. One embodiment employs 100% oxygen, in another embodiment the 100% oxygen is administered at 1.3-1.4 atmospheres pressure.

Long Term Treatment

As noted above, a bipolar trans carotenoid such as TSC can improve oxygen conditions in tissues of a mammal having PVD. Further, preconditioning with a bipolar trans carotenoids also can significantly reduce the volume of tissue damage after a period of ischemic (see Example 2). Lastly, many PVD cases are due to atherosclerotic change. A bipolar trans carotenoid can also reduce the formation of atherosclerotic plaque and thus is beneficial in treating PVD in the long term.

The bipolar trans carotenoid can be administered by injection (intravenous or intramuscular) or infusion, or by pulmonary, oral or transdermal routes for extended periods of time, e.g. 5 or more days, weeks, months or years. For a dose to be "therapeutically effective" it must have the desired effect, i.e. in the case of PVD, that amount which reduces symptoms and/or increases the level of oxygen in the peripheral arteries and veins. A typical daily dose is from 0.05 to 5.0 mg/kg in humans, advantageously from 0.1 to 3.5 mg/kg.

A bipolar trans carotenoid such as TSC can be combined with the oxygen treatment and cause even more oxygen to reach the tissues. One method for doing this employs 100% oxygen at ambient pressure or 1.3-1.4 atmospheres pressure.

Administration of a bipolar trans carotenoid such as TSC, using the therapy listed above, is also a beneficial treatment for ischemia, such as cerebral ischemia or peritoneal ischemia, coronary artery disease, myocardial infarction and angina. The compounds of the invention as administered above are also useful in the treatment of ischemic osteonecrosis or for treating chronic ocular disease including glaucoma, macular degeneration, and diabetic retinopathy.

The bipolar trans carotenoid, such as TSC, can be administered by injection (intravenous or intramuscular) or infusion, or by pulmonary, oral or transdermal routes for a short time, e.g. 1-24 hours or 1-4 days, or extended periods of time, e.g. 5 or more days, weeks, months or years. For a dose to be "therapeutically effective" it must have the desired effect, i.e., that amount which reduces symptoms and/or increases the level of oxygen in the affected area. A typical daily dose is from 0.05 to 5.0 mg/kg in humans, advantageously from 0.1 to 3.5 mg/kg.

A bipolar trans carotenoid such as TSC can be combined with the oxygen treatment and cause even more oxygen to reach the tissues. One method for doing this employs 100% oxygen at 1.3-1.4 atmospheres pressure.

Use of a Bipolar Trans Carotenoid as a Pretreatment to Prevent or Reduce the Impact of an Ischemic Event Administration of a bipolar trans carotenoid such as TSC to a patient is a beneficial treatment prior to an ischemic event or a hypoxic event, such as a significant blood loss. A bipolar trans carotenoid can be used prophylactically whenever blood flow is subsequently diminished. Such decrease in blood flow can occur after blood is lost through hemorrhage or if a blockage or constriction of an artery or vein occurs. The patients to be treated include patients who are experiencing no symptoms related to disease.

Although trans sodium crocetinate (TSC) was developed for the treatment of hypoxic (low oxygen) situations, studies have been done to assess its effectiveness for preventing or lessening damage if given prior to the hypoxic insult.

Pretreatment is most often thought of as a preventative treatment, and is common with chronic ailments. For example, one might take antihypertensive agents and/or lipid-lowering drugs in order to prevent a heart attack. The logic behind this therapy is to treat two of the conditions (high blood pressure and elevated serum lipids) which are closely associated with heart attack in order to prevent it from occurring. Pretreatment is not usually associated with acute diseases or conditions. However, there are cases where it is, and a bipolar trans carotenoid pretreatment in such cases is discussed herein. TSC has been used to prevent ischemic damage. TSC can reduce the damage to tissues occurring from a hypoxic event which occurs after being treated with TSC.

Preconditioning or pretreating a patient (mammal including human) with a bipolar trans carotenoid is advisable for the following patients:

a patient at risk of an ischemic event;

a patient at risk of forming an embolism or blood clot in the blood vessels, the brain, the heart, or the lungs. The embolism can be fat globules (a fat embolism), air bubbles (an air embolism), talc embolism (often following drug abuse), septic emboli (containing pus and bacteria), atherosclerotic emboli, or amniotic fluid;

a patient at risk of stroke including a patient diagnosed with a blocked carotid artery or having suffered a transient ischemic attack (TIA). In Example 2, TSC was administered intravenously to rats 24 hours before the ischemic injury to the brain occurred. Sufficient time passed between the administration of TSC and the subsequent event so that the TSC would have been cleared from the system. The TSC was dissolved in water, and given over a period of an hour in the following manner. First a 0.1 ml bolus injection was given, then a slow infusion (0.6 ml given over 60 minutes) was given, and finally another 0.1 ml bolus was given. The total TSC dosage administered was 0.091 mg/kg. Twenty-four hours after the TSC administration, a focal ischemia in the brain was induced by occluding both of the carotid arteries and the middle cerebral artery. The occlusions were removed after 2 hours, and the infarct volume (core plus penumbra) was measured 24 hours later. Pretreatment with TSC twenty-four hours in advance of the induced stroke resulted in a large reduction in the amount of brain tissue that was ischemic, and the result is statistically significant (p<0.01). An intraischemic treatment with TSC done previously resulted in a 58% reduction in infarct volume in this model. This preischemic treatment resulted in a 65% reduction in infarct volume—a similar result;

a patient at risk of suffering a myocardial infarct, including a patient who has had a myocardial infarct, particularly a patient who has had a myocardial infarct within the last three months;

a patient with a prosthetic valve;

a patient with mitral valve disease, or with mitral valve stenosis with atrial fibrillation;

a patient diagnosed with atherosclerosis;

a patient taking a drug that increases the risk of clot formation a patient who may lose significant blood, including a soldier prior to battle;

a patient who has had surgery and is in danger of forming a clot or embolism;

a patient who has had an embolism;

a patient who will be put on a heart and lung machine;

a patient who will be put on a dialysis machine;

a patient with constricted arteries or veins.

For all of the above situations, the patient at risk of an ischemic event can have no symptoms relating to ischemia at the time of the treatment.

As a pretreatment (prophylactic), the bipolar trans carotenoid can be administered by injection (intravenous or intramuscular) or infuse for a short time (e.g.s 45 minutes-24 hours, or 1-4 days) leading up to a possible ischemic event, or for extended periods of time, e.g. 5 or more days, weeks, months or years leading up to a possible ischemic event. For a dose to be "therapeutically effective" it must have the desired effect, i.e. that amount which would reduce or prevent damage if an ischemic event should occur. A typical daily dose is from 0.05 to 5.0 mg/kg in humans, advantageously from 0.1 to 3.5 mg/kg.

As a pretreatment, a bipolar trans carotenoid such as TSC can be combined with the oxygen treatment and cause even more oxygen to reach the tissues. One method for doing this employs 100% oxygen at 1.3-1.4 atmospheres pressure.

Compounds and Compositions of the Invention

The compounds of the subject invention are trans carotenoids including trans carotenoid diesters, dialcohols, diketones and diacids, bipolar trans carotenoids (BTC), and bipolar trans carotenoid salts (BTCS) having the structure:

YZ-TCRO-ZY where:

Y (which can be the same or different at the two ends)=H or a cation other than H, preferably $Na^+$ or $K^+$ or $Li^+$. Y is advantageously a monovalent metal ion. Y can also be an organic cation, e.g., $R_4N^+$, $R_3S^+$, where R is H, or $C_nH_{2n+1}$ where n is 1-10, advantageously 1-6. For example, R can be methyl, ethyl, propyl or butyl.

Z (which can be the same or different at the two ends)=polar group which is associated with H or the cation. Optionally including the terminal carbon on the carotenoid (or carotenoid related compound), this group can be a carboxyl ($COO^-$) group or a CO group (e.g. ester, aldehyde or ketone group), or a hydroxyl group. This group can also be a sulfate group ($OSO_3^-$) or a monophosphate group ($OPO_3^-$), ($OP(OH)O_2^-$), a diphosphate group, triphosphate or combinations thereof. This group can also be an ester group of COOR where the R is $C_nH_{2n+1}$.

TCRO=trans carotenoid or carotenoid related skeleton (advantageously less than 100 carbons) which is linear, has pendant groups (defined below), and typically comprises "conjugated" or alternating carbon-carbon double and single bonds (in one embodiment, the TCRO is not fully conjugated as in a lycopene). The pendant groups (X) are typically methyl groups but can be other groups as discussed below. In an advantageous embodiment, the units of the skeleton are joined in such a manner that their arrangement is reversed at the center of the molecule. The 4 single bonds that surround a carbon-carbon double bond all lie in the same plane. If the pendant groups are on the same side of the carbon-carbon double bond, the groups are designated as cis (also known as "Z"); if they are on the opposite side of the carbon-carbon bond, they are designated as trans (also known as "E"). Throughout this case, the isomers will be referred to as cis and trans.

The compounds of the subject invention are trans. The cis isomer typically is a detriment—and results in the diffusivity not being increased. In one embodiment, a cis isomer can be utilized where the skeleton remains linear. The placement of the pendant groups can be symmetric relative to the central point of the molecule or can be asymmetric so that the left side of the molecule does not look the same as the right side of the molecule either in terms of the type of pendant group or their spatial relationship with respect to the center carbon.

The pendant groups X (which can be the same or different) are hydrogen (H) atoms, or a linear or branched hydrocarbon group having 10 or less carbons, advantageously 4 or less, (optionally containing a halogen), or a halogen. X could also be an ester group (COO—) or an ethoxy/methoxy group. Examples of X are a methyl group ($CH_3$), an ethyl group ($C_2H_5$), a phenyl or single aromatic ring structure with or without pendant groups from the ring, a halogen-containing alkyl group (C1-C10) such as $CH_2Cl$, or a halogen such as Cl or Br or a methoxy ($OCH_3$) or ethoxy ($OCH_2CH_3$). The pendant groups can be the same or different but the pendant groups utilized must maintain the skeleton as linear.

Although many carotenoids exist in nature, carotenoid salts do not. Commonly-owned U.S. Pat. No. 6,060,511 hereby incorporated by reference in its entirety, relates to trans sodium crocetinate (TSC). The TSC was made by reacting naturally occurring saffron with sodium hydroxide followed by extractions that selected primarily for the trans isomer.

The presence of the cis and trans isomers of a carotenoid or carotenoid salt can be determined by looking at the ultraviolet-visible spectrum for the carotenoid sample dissolved in an aqueous solution. Given the spectrum, the value of the absorbence of the highest peak which occurs in the visible wave length range of 380 to 470 nm (the number depending on the solvent used and the chain length of the BTC or BTCS. The addition of pendant groups or differing chain lengths may change this peak absorbance but someone skilled in the art will recognize the existence of an absorbance peak in the visible range corresponding to the conjugated backbone structure of these molecules.) is divided by the absorbency of the peak which occurs in the UV wave length range of 220 to 300 nm can be used to determine the purity level of the trans isomer. When the trans carotenoid diester (TCD) or BTCS is dissolved in water, the highest visible wave length range peak will be at between 380 nm to 470 nm (depending on the exact chemical structure, backbone length and pendant groups) and the UV wave length range peak will be between 220 to 300 nm According to M. Craw and C. Lambert, Photochemistry and Photobiology, Vol. 38 (2), 241-243 (1983) hereby incorporated by reference in its entirety, the result of the calculation (in that case crocetin was analyzed) was 3.1, which increased to 6.6 after purification.

Performing the Craw and Lambert analysis, using a cuvette designed for UV and visible wavelength ranges, on the trans sodium salt of crocetin of commonly owned U.S. Pat. No. 6,060,511 (TSC made by reacting naturally occurring saffron with sodium hydroxide followed by extractions which selected primarily for the trans isomer), the value obtained averages about 6.8. Performing that test on the synthetic TSC of the subject invention, that ratio is greater than 7.0 (e.g. 7.0 to 8.5), advantageously greater than 7.5 (e.g. 7.5-8.5), most advantageously greater than 8. The synthesized material is a "purer" or highly purified trans isomer.

Advantageously, the trans carotenoid is crocetin, crocin, a bipolar trans carotenoid (BTC) salt such as TSC, or a carotenoid diester, alcohol or acid.

The bipolar trans carotenoid can be formulated in a variety of ways. See commonly owned application U.S. patent application Ser. No. 10/647,132, hereby incorporated by reference in its entirety, and commonly owned U.S. patent application Ser. No. 11/361,054, hereby incorporated by reference in its entirety.

Advantageously, the bipolar trans carotenoid is in the form of a composition comprising a trans carotenoid and a cyclodextrin, for example alpha cyclodextrin, beta cyclodextrin or gamma cyclodextrin. The cyclodextrin can be hydroxylpropyl-beta-cyclodextrin or 2-hydroxylpropyl-gamma-cyclodextrin. In another embodiment, the composition further comprises mannitol or saline. In a still further embodiment, the composition further comprises a compound to regulate pH such as bicarbonate or glycine.

In another embodiment the composition is lyophilized, i.e. a lyophilized composition of a bipolar trans carotenoid such as TSC, or the bipolar trans carotenoid can be crystallized.

The following examples are illustrative, but not limiting of the compounds, compositions and methods of the present invention. Other suitable modifications, and adaptations of a variety of conditions and parameters normally encountered which are obvious to those skilled in the art are within the spirit and scope of the invention.

EXAMPLES

Example 1

TSC Causes Increase in the TCOM Reading

For the rat TCOM studies, male Sprague-Dawley rats were used which weighed between 350 and 400 grams each. TCOM electrodes are attached to humans on the chest, on the leg, or on the top of the foot. Using a TCOM apparatus (Radiometer), the electrodes were attached to the shaven skin in the areas of the chest, the abdomen, and the thigh of the rats. Pure oxygen was then administered to the rats. The most reproducible results came from the electrode attached near the rat's abdomen, on the left or right side.

The rats were anesthetized (to quiet them) using IP injections of 80 mg/kg ketamine and 10 mg/kg xylazine.

After the animals were asleep, the abdomen area of the rat was shaved and the TCOM electrode collar was attached to that area. Using Dow Corning high vacuum silicone grease between the electrode collar and the skin was helpful in maintaining a good seal on the rat's skin.

After attaching the TCOM probe, the transcutaneous oxygen tension was then monitored for 30 minutes while the rat breathed room air. The rat was then switched to 100% oxygen and TSC was injected into the femoral vein. The TCOM readings were then recorded for an additional 45 minutes. That last 45 minutes is shown in FIG. 1, and it can be seen that TSC causes an additional increase in the TCOM reading during that time.

Example 2

Ischemic Tolerance Induced by Trans-Sodium Crocetinate in Focal Cerebral Ischemic Model Trans-sodium crocetinate (0.091 mg/kg total dosage) or vehicle was administered intravenously as follows 1) 0.1 ml injection 2) continuous infusion of TSC at a rate of 0.01 ml/min for the next 60 minutes, and 3) a final 0.1 ml injection of TSC 30 minutes after the cessation of continuous infusion. Twenty-four hours later, the animals were subjected to a transient period of ischemia (120 minutes) by occluding simultaneously both common carotid arteries (CCA) and the middle cerebral artery (MCA). Infarction volumes were measured 24 hours after the ischemic event.

The effects of TSC on focal ischemic injury were examined using adult male Sprague-Dawley rats, each of which weighed between 330 and 370 g. All procedures were approved by the University of Virginia Animal Care Committee. The animals were initially anesthetized in a chamber with a mixture of 4% halothane in oxygen gases. After being completely anesthetized, orotracheal intubation was performed and orotracheal tube was connected to a ventilator (Rodent Ventilator model 638, Harvard Apparatus, Holliston, Mass.). The right femoral artery and vein was cannulated for blood pressure monitoring, repeated blood gas analysis (348 Blood Gas Analyzer, Bayer HealthCare, Tarrytown, N.Y.) and infusion of drug. Rectal temperature was monitored continuously and maintained at 37° C. with a heating lamp. During the operation, the concentration of halothane was controlled around 1.5% in N2:O2 (50%:50%) to keep the mean arterial blood pressure around 110 mmHg.

Three Vessel Occlusion Model:

Focal ischemic was performed by clipping (Sundt AVM microclip No 1, Codman & Shurtleff, Inc., Raynham, Mass.) the MCA at a point distal to the origin of the lenticulostriate arteries. The polypropylene suture loops around both CCAs were closed at the same time. Loss of blood flow was confirmed visually. The microclip on MCA and polypropylene snares around both CCAs were removed 120 minutes after ischemic onset and recirculation was confirmed by observing directly. After 24 hours, infarct volume was calculated.

24 hours after ischemic onset, animals were anesthetized with an over dose of pentobarbital and killed by decapitation. The brains were removed rapidly and 2 mm thickness of coronal sections were cut with a McIlwain tissue chopper and stained in 2% 2,3,5 triphenyltetrazorium chloride (TTC) in phosphate-buffered saline for 5 min at 37° C. and then placed in 10% paraformaldehyde solution. Infarction volume was calculated by summing the infarction areas in individual sections using image analysis software (Scion Image Beta 4.02, Scion Corporation, Frederick, Md.). In addition, the areas of the hemispheres ipsilateral and contralateral to the occluded MCA were measured, and the total volume of each hemisphere was calculated in similar manner. The actual infarct volume, adjusted for swelling, was calculated using the following formula: total infarct volume×(contralateral hemisphere volume/ipsilateral hemisphere volume). The values shown in both text and figures are the calculated actual infarct volume.

Results:

Three-vessel occlusion (3VO) elicited cerebral infarction volumes in the 3VO-only and 3VO+Vehicle groups of 165.6±47.2 mm3 and 133.9±17.5 mm3 (mean±SEM), respectively. The infarct volumes in these two groups did not differ significantly (one-way ANOVA). Trans-sodium crocetinate reduced infarct volume substantially. Infarct volume in the 3VO+TSC group was 57.7±16.2 mm3. This decrease in infarct volume achieved statistical significance when the 3VO+TSC group was compared to either the 3VO-only or 3VO+Vehicle group ($p<0.01$, one-way ANOVA with the Holm-Sidak post hoc test).

Figure 2:
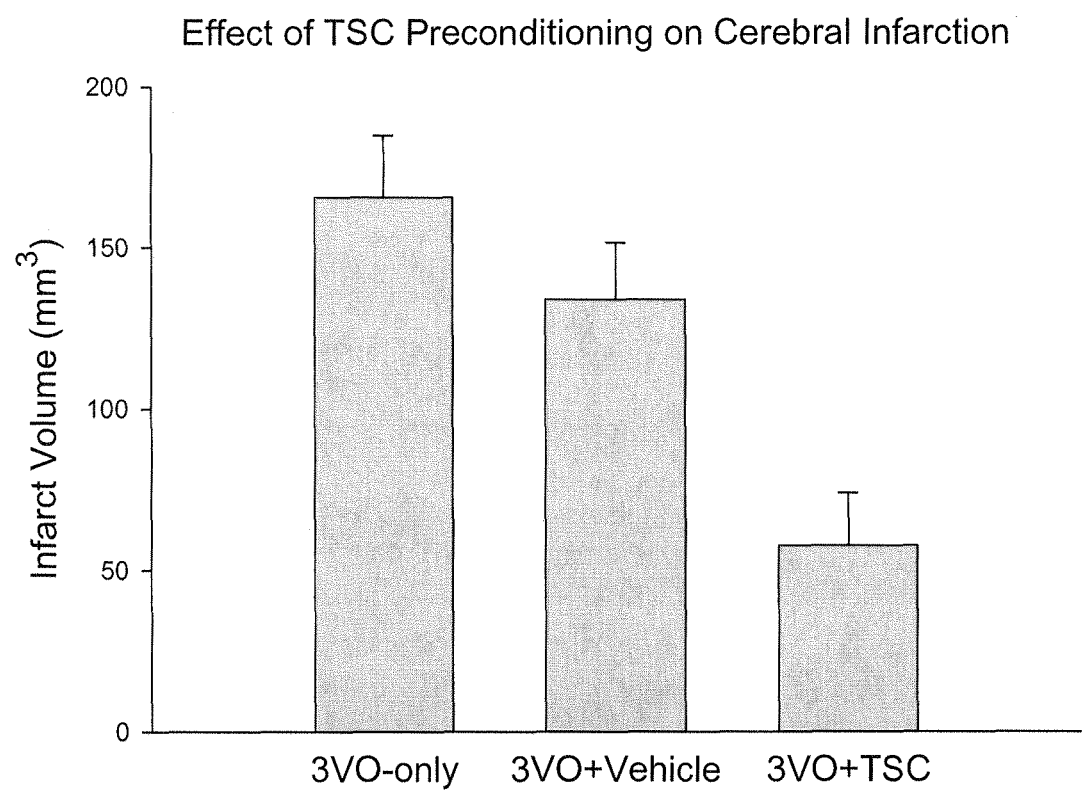
FIG. 2 is a graph of Effect of TSC Preconditioning of Cerebral Infarction.

FIG. 2 shows the results comparing three groups: 3VO-only (rats receiving no pretreatment but having their three arteries occluded), 3VO+Vehicle (rats receiving an injection minus TSC and having their three arteries occluded), 3VO+TSC (rats receiving a pretreatment injection of TSC and having their three arteries occluded).

It will be readily apparent to those skilled in the art that numerous modifications and additions can be made to both the present compounds and compositions, and the related methods without departing from the invention disclosed.

What is claimed is:

1. A method of treating a mammal having angina comprising administering a therapeutically effective amount of a bipolar trans carotenoid salt having the structure:

YZ-TCRO-ZY where
Y=a cation which can be the same or different,
Z=a polar group which can be the same or different and which is associated with the cation, and
TCRO=a linear trans carotenoid skeleton with conjugated carbon-carbon double bonds and single bonds and having pendant groups X, wherein the pendant groups X, which can be the same or different, are (1) a linear or branched hydrocarbon group having 10 or less carbon atoms, or (2) a halogen.

2. A method of treating ischemic osteonecrosis or peritoneal ischemia comprising: administering a therapeutically effective amount of a bipolar trans carotenoid salt having the structure:

YZ-TCRO-ZY where
Y=a cation which can be the same or different,
Z=a polar group which can be the same or different and which is associated with the cation, and
TCRO=a linear trans carotenoid skeleton with conjugated carbon-carbon double bonds and single bonds and having pendant groups X, wherein the pendant groups X, which can be the same or different, are (1) a linear or branched hydrocarbon group having 10 or less carbon atoms, or (2) a halogen.

3. A method of treating chronic ocular disease, macular degeneration, or diabetic retinopathy comprising: administering a therapeutically effective amount of a bipolar trans carotenoid salt having the structure:

YZ-TCRO-ZY where
Y=a cation which can be the same or different,
Z=a polar group which can be the same or different and which is associated with the cation, and
TCRO=a linear trans carotenoid skeleton with conjugated carbon-carbon double bonds and single bonds and having pendant groups X, wherein the pendant groups X, which can be the same or different, are (1) a linear or branched hydrocarbon group having 10 or less carbon atoms, or (2) a halogen.

4. A method of reducing the formation of atherosclerotic plaque in a mammal having atherosclerotic plaque comprising:
administering a therapeutically effective amount of a bipolar trans carotenoid salt having the structure:

YZ-TCRO-ZY where
Y=a cation which can be the same or different,
Z=a polar group which can be the same or different and which is associated with the cation, and
TCRO=a linear trans carotenoid skeleton with conjugated carbon-carbon double bonds and single bonds and having pendant groups X, wherein the pendant groups X, which can be the same or different, are (1) a linear or branched hydrocarbon group having 10 or less carbon atoms, or (2) a halogen.

5. A method as in claim 1, 2, 3, or 4 wherein the bipolar trans carotenoid salt is administered by intravenous administration.

6. A method as in claim 1, 2, 3 or 4 wherein the bipolar trans carotenoid salt is administered by IM, oral, pulmonary or transdermal administration.

7. A method as in claim 1, 2, 3 or 4 further comprising administering oxygen to said mammal.

8. A method as in claim 1, 2, 3 or 4 wherein the bipolar trans carotenoid salt comprises trans sodium crocetinate.

9. A method as in claim 1, 2, 3 or 4 wherein said bipolar trans carotenoid salt is in the form of a composition comprising a bipolar trans carotenoid salt and a cyclodextrin.

10. A method as in claim 1, 2, 3 or 4 wherein Y is a monovalent metal ion selected from the group consisting of Na+ or K+ or Li+, or an organic cation selected from the group consisting of R4 N+ or R3 S+ where R is H, and CnH2n−1 where n is 1-10.

11. A method as in claim 1, 2, 3 or 4 wherein Z is selected from the group consisting of a carboxyl (COO—) group, a CO group, a hydroxyl group, a sulfate group (OSO3-), a monophosphate group (OPO3-) or (OP(OH)O2-), a diphosphate group, a triphosphate, and combinations thereof.

12. A method as in claim 1, 2, 3 or 4 wherein Y is Na+, Z is a carboxyl (COO—) group, and X is a methyl group.

13. A method as in claim 1, 2, 3 or 4 wherein the mammal is a human.

14. A method as in claim 9 wherein the cyclodextrin is alpha cyclodextrin.

15. A method as in claim 9 wherein the cyclodextrin is beta cyclodextrin.

16. A method as in claim 9 wherein the cyclodextrin is 2-hydroxylpropyl-beta-cyclodextrin.

17. A method as in claim 9 wherein the cyclodextrin is gamma cyclodextrin.

18. A method as in claim 9 wherein the cyclodextrin is 2-hydroxylpropyl-gamma-cyclodextrin.

19. A method as in claim 9 wherein said composition further comprises mannitol.

20. A method as in claim 9 wherein said composition further comprises saline.

21. A method as in claim 9 wherein said composition further comprises a compound to regulate pH.

22. A method as in claim 21 wherein said compound to regulate pH is selected from the group consisting of a buffer such as bicarbonate or glycine.

23. A method as in claim 9 wherein said composition is lyophilized or crystallized.

24. A method as in claim 9 wherein said composition comprises a lyophilized or crystallized composition of a bipolar trans carotenoid salt.

\* \* \* \* \*